United States Patent [19]

Hamanaka

[11] Patent Number: 4,772,597
[45] Date of Patent: Sep. 20, 1988

[54] 2-AZACYCLOALKYLTHIOPENEM DERIVATIVES

[75] Inventor: Ernest S. Hamanaka, Gales Ferry, Conn.

[73] Assignee: Pfizer Inc., New York, N.Y.

[21] Appl. No.: 649,516

[22] Filed: Sep. 13, 1984

Related U.S. Application Data

[63] Continuation-in-part of Ser. No. 542,310, Oct. 14, 1983, abandoned.

[51] Int. Cl.$^4$ .................. C07D 499/00; A61K 31/425
[52] U.S. Cl. .................................. 514/192; 514/195; 540/310
[58] Field of Search .................. 260/245.2 R, 245.2 T; 514/196, 192, 195; 540/310

[56] References Cited

U.S. PATENT DOCUMENTS

| | | | |
|---|---|---|---|
| 4,260,618 | 4/1981 | Christensen et al. | 514/192 |
| 4,435,412 | 3/1984 | Girryavallabhan et al. | 424/270 |
| 4,435,413 | 3/1984 | McCombie | 424/270 |
| 4,456,609 | 6/1984 | McCombie | 424/270 |
| 4,530,793 | 7/1985 | Girijavallabhan | 540/310 |
| 4,613,595 | 9/1986 | Miyadea | 540/310 |
| 4,614,737 | 9/1986 | Hamanaka | 540/310 |
| 4,614,738 | 9/1986 | Girijavallabhan | 540/310 |
| 4,675,317 | 6/1987 | DiNinno et al. | 540/310 |

FOREIGN PATENT DOCUMENTS

| | | |
|---|---|---|
| 0070204 | 1/1983 | European Pat. Off. . |
| 7176988 | 10/1982 | Japan . |
| 2104075A | 3/1983 | United Kingdom . |

OTHER PUBLICATIONS

S. Oida et al., Tetrahedron Letters, vol. 21, pp. 619–620 (1980).
M. Alpegiani et al., Heterocycles, 23, pp. 2255–2270 (1985).
G. Emmer et al., Jour. Antibiotics, XXXVIII, pp. 1371–1386 (1985).
G. Franceschi et al., Jour. Antibiotics, XXXVII, pp. 685–688 (1984).

*Primary Examiner*—Nicholas S. Rizzo
*Attorney, Agent, or Firm*—Peter C. Richardson; Albert E. Frost; Gregg C. Benson

[57] ABSTRACT

Certain 2-azacycloalkylthio-2-penem-3-carboxylic acid compounds are useful as antibacterials for treating mammals and have the formula

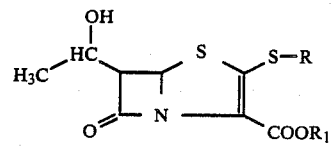

or a pharmaceutically acceptable salt thereof, wherein:
R is

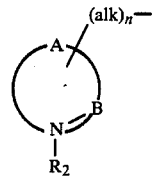

A is alkylene having 2–4 carbon atoms, alkylene having 2–4 carbon atoms wherein a carbon atom has an oxo substituent or alkylene having 2–4 carbon atoms wherein a methylene is replaced by oxygen, $S(O)_m$, or $N-R_3$;
B is carbonyl, thiocarbonyl, methylene or imine;
$R_1$ is hydrogen or forms an ester group which is hydroyzed in vivo;
$R_2$ is hydrogen, formyl, alkylcarbonyl, N-alkylaminocarbonyl, N-alkylaminosulfonyl, aminosulfonyl, aminocarbonyl, alkoxycarbonyl having 2–5 carbon atoms, alkylsulfonyl, alkyl, or alkyl substituted by aminocarbonyl, alkyl—$S(O)_m$—, hydroxyl, amino, alkylcarbonylamino, formamido or alkylsulfonylamino, wherein each alkyl has 1–4 carbon atoms;
$R_3$ is hydrogen, methyl, formyl, methylcarbonyl or methylsulfonyl;
alk is alkylene having 1–4 carbon atoms;
n is zero or one; and
m is zero, 1 or 2.

24 Claims, No Drawings

2-AZACYCLOALKYLTHIOPENEM DERIVATIVES

RELATED COPENDING APPLICATION

This application is a continuation-in-part of Ser. No. 542,310, filed Oct. 14, 1983 and now abandoned.

BACKGROUND OF THE INVENTION

This invention is directed to a family of antibacterial agents incorporating a 2-azetidinone (betalactam) ring. Chemically, the antibacterial agents of this invention are identified as 6-alpha-1-hydroxyethyl-2-substituted-2-penem-3-carboxylic acid compounds.

Although certain 2-substituted-2-penem-3-carboxylic acid compounds have been previously disclosed, there is a continuing need for novel compounds having desirable antibacterial therapeutic properties.

SUMMARY OF THE INVENTION

The present invention is directed to a compound of the formula

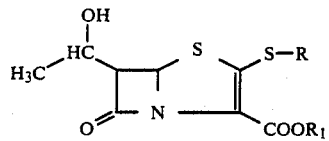

or a pharmaceutically acceptable salt thereof, wherein: R is

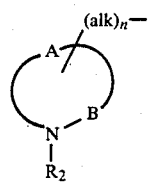

A is alkylene having 2-4 carbon atoms, alkylene having 2-4 carbon atoms wherein a carbon atom has an oxo substituent or alkylene having 2-4 carbon atoms wherein a methylene is replaced by oxygen, $S(O)_m$, or $N—R_3$;

B is carbonyl, thiocarbonyl, methylene or imine;

$R_1$ is hydrogen or forms an ester group which is hydrolyzed in vivo;

$R_2$ is hydrogen, formyl, alkylcarbonyl, N-alkylaminocarbonyl, N-alkylaminosulfonyl, aminosulfonyl, aminocarbonyl, alkoxycarbonyl having 2-5 carbon atoms, alkylsulfonyl, alkyl, or alkyl substituted by aminocarbonyl, alkyl—$S(O)_m$—, hydroxyl, amino, alkylcarbonylamino, formamido or alkylsulfonylamino, wherein each alkyl has 1-4 carbon atoms;

$R_3$ is hydrogen, methyl, formyl, methylcarbonyl or methylsulfonyl;

alk is alkylene having 1-4 carbon atoms;

n is zero or one; and m is zero, 1 or 2.

Included within the scope of the present invention is a compound of the formula

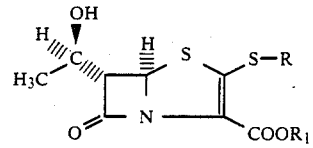

or a pharmaceutically acceptable salt thereof, wherein:
R is as defined above for compounds of formula I.

Preferred compounds of formulae I and II include those wherein A is alkylene, B is carbonyl, $R_2$ is hydrogen or methyl and n is zero. Particularly preferred are compounds wherein $R_1$ is hydrogen and R is 2-pyrrolidon-3-yl, 2-pyrrolidon-4-yl, piperidin-2-on-3-yl, 1-methyl-piperidin-2-on-3-yl, or 2-piperidon-5-yl.

Also preferred are compounds where A is alkylene, B is methylene, $R_2$ is formyl and n is zero. Particularly preferred is the compound wherein $R_1$ is hydrogen and R is 1-formyl-3-pyrrolidinyl or 1-formylpiperidin-3-yl.

Further preferred are compounds wherein A is carbonylethylene or carbonylpropylene, B is carbonyl, $R_2$ is hydrogen or methyl, with the proviso that the ethylene or propylene of A is bonded to B; particularly the compounds wherein $R_1$ is hydrogen and R is pyrrolidin-2,5-dion-3-yl.

Additionally preferred are compounds where A is 1-oxaalkylene, B is carbonyl, $R_2$ is hydrogen or methyl and n is one, with the proviso that the oxygen of 1-oxaalkylene is bonded to B; particularly wherein $R_1$ is hydrogen and R is (3-methyl-1,3-oxazolidin-2-on-4-yl)methyl, (3-methyl-1,3-oxazolidin-2-on-5-yl)methyl, (1,3-oxazolidin-2-on-4-yl)methyl, or (1,3-oxazolidin-2-on-5-yl)methyl.

Embraced by the present invention are compounds wherein A is 1-oxaalkylene and B is carbonyl, $R_2$ is hydrogen or methyl and n is zero; particularly when $R_1$ is hydrogen and R is 3-methyl-perhydro-1,3-oxazolidin-2-on-5-yl.

Also embraced by the present invention are compounds wherein A is 1-thiaalkylene, B is carbonyl, $R_2$ is hydrogen or methyl and n is one; particularly when $R_1$ is hydrogen and R is (1,3-thiazolidin-2-on-4-yl)methyl.

Further embraced by the present invention is a pharmaceutical composition comprising a compound of formula I or II and a pharmaceutically acceptable diluent or carrier; and a method of treating a bacterial infection in a mammal comprising administering an antibacterially effective amount of a compound of formula I or II.

DETAILED DESCRIPTION OF THE INVENTION

The compounds of formulae I and II are useful as antibacterial agents, and are derivatives of the bicyclic nucleus of the formula:

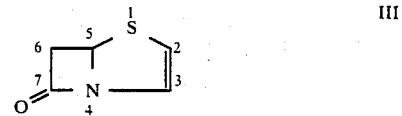

Throughout this specification, the nucleus of formula III is identified by the name "2-penem," and ring atoms are numbered as shown. The carbon atom attached to ring carbon 6 is given the number 8. Also, throughout this specification, the abbreviation "PNB" is used for the p-nitrobenzyl group.

The relationship between the hydrogen on bridgehead carbon 5 and the remaining hydrogen on carbon 6 in compounds of formula I can either be cis or trans. The present invention embraces both isomers as well as mixtures thereof. The trans isomer is generally preferred in pharmaceutical applications and the cis isomer can be readily converted to the trans-isomer.

Generally, carbon 5 will have the absolute stereochemistry designated R using the Prelog-Ingold R, S stereochemical notation, which is employed in this application. Thus, for example, a compound of formula II wherein $R_1$ is hydrogen and R is 2-pyrrolidon-3-yl is named (5R,6S)-6-[(R)-1-hydroxyethyl]-2-(2-pyrrolidon-3-yl)thio-3-carboxyl-2-penem.

As will be appreciated, various optically active isomers of the new compounds are possible. The present invention embraces such optically active isomers as well as mixtures thereof.

The present invention includes those penems in which the 3-carboxyl group is esterified with a nontoxic ester group which is hydrolyzed in vivo. These esters are rapidly cleaved in mammalian blood or tissue to release the corresponding penem-3-carboxylic acid. Typical examples of such readily hydrolyzable ester-forming residues are alkanoyloxymethyl having from 3-8 carbon atoms, 1-(alkanoyloxy)ethyl having from 4-9 carbon atoms, 1-methyl-1-(alkanoyloxy)ethyl having from 5-10 carbon atoms, alkoxycarbonyloxymethyl having from 3-6 carbon atoms, 1-(alkoxycarbonyloxy)ethyl having from 4-7 carbon atoms, 1-methyl-1-(alkoxycarbonyloxy)ethyl having from 5-8 carbon atoms, N-(alkoxycarbonyl)aminomethyl having from 3-9 carbon atoms, 1-(N-[alkoxycarbonyl]amino)ethyl having from 4-10 carbon atoms, 3-phthalidyl, 4-crotonolactonyl, gamma-butyrolacton-4-yl, carboxyalkylcarbonyloxymethyl having from 4-12 carbon atoms, or 5-methyl-2-oxo-1,3-dioxolen-4-yl-methyl.

To prepare compounds of formula I or II wherein $R_1$ is a group which forms an ester which is hydrolyzed in vivo, the acid of formula I or II ($R_1$ is hydrogen) is reacted with a base to form the corresponding anion. Suitable cations include sodium, potassium, calcium, tetra-alkylammonium and the like. The anion can be prepared by lyophilizing an aqueous solution of I or II, for example, an aqueous solution containing tetrahydrofuran, and sodium bicarbonate or tetrabutylammonium hydroxide.

The resulting anion of I or II is reacted with the corresponding chloride or bromide of $R_1$ in a reaction-inert solvent such as acetone or dimethylformamide at about 20° to about 50° C., preferably 25° C.

The compounds of formula II can be synthesized according to Schemes A-C.

As shown in Scheme A, a compound of formula II can be prepared in accordance with the procedure of Yoshida et al, Chem. Pharm. Bull., 29, 2899-2909(1981), from the known dibromo penam of formula IV. The dibromo penam (IV) undergoes an exchange reaction with t-butyl magnesium chloride at a temperature of between about −90° and −40° C., preferably about −78° C. in a reaction-inert solvent such as tetrahydrofuran, diethyl ether or toluene, preferably tetrahydrofuran. Other organometallic reagents may also be employed. The resultant reaction mixture is treated in situ with the appropriate aldehyde; e.g., acetaldehyde for the 1-hydroxyethyl derivative. The aldehyde is added at between about −80° and −60° C., preferably about −78° C. for acetaldehyde.

The resulting bromo hydroxy penam V is hydrogenated to remove the 6-bromo substituent. A suitable hydrogenation catalyst is a noble metal catalyst such as palladium. The reaction is carried out in a protic solvent such as 1:1 methanol-water or 1:1 tetrahydrofuran-water, preferably 1:1 methanol-water, at a pressure of about 1 to 4 atms, preferably 4 atm and a temperature of between about 0° and 30° C., preferably about 25° C.

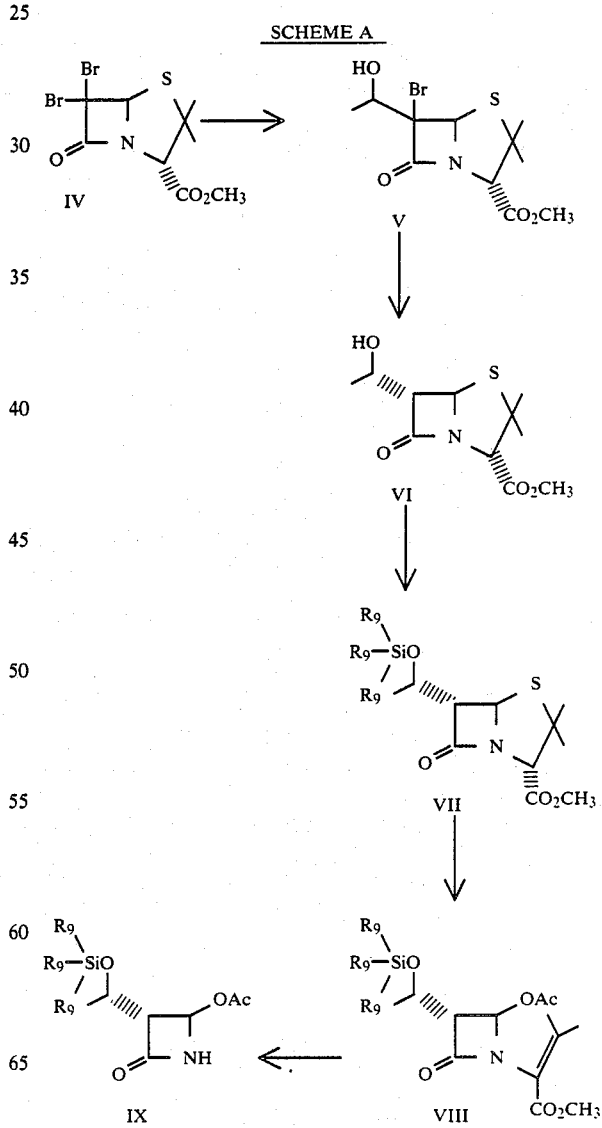

SCHEME A

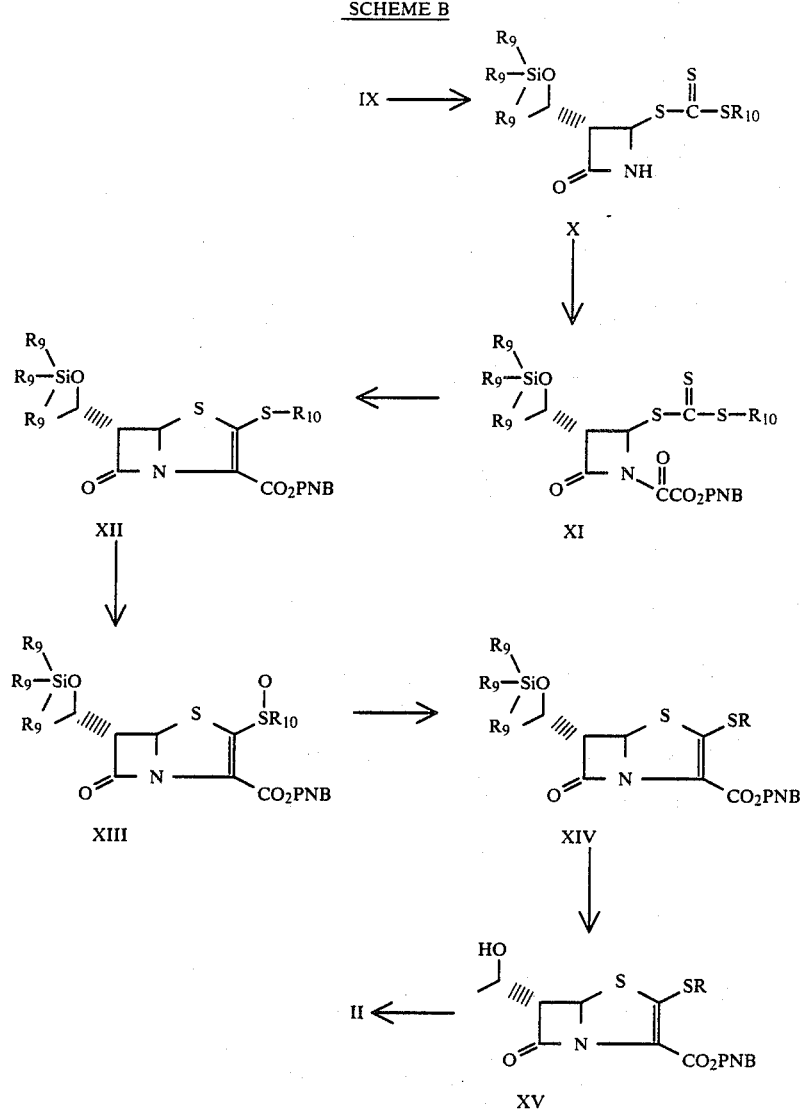
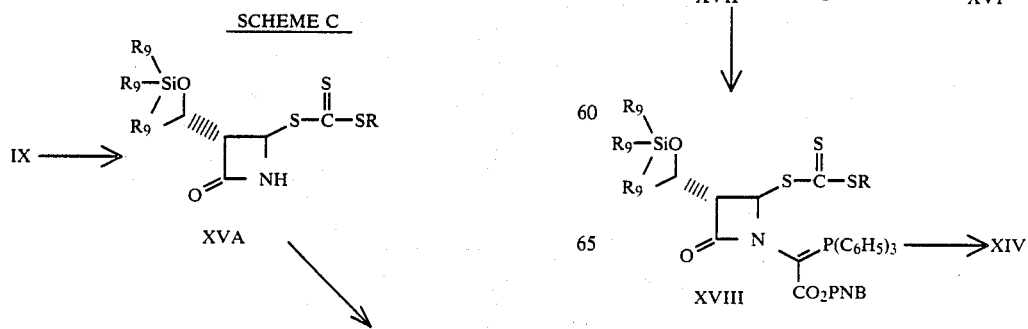

The resulting alcohol of formula VI can be protected with a trialkylhalosilane of formula

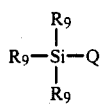

wherein $R_9$ at each occurrence is an alkyl of 1 to 6 carbon atoms and Q is chloro, bromo or iodo. Thus, dimethyl-t-butylchlorosilane in the presence of an amine proton acceptor, such as imidazole, in a polar, aprotic solvent such as N,N-dimethylformamide at a temperature range of between about 5° and 40° C., preferably about 25° C., forms a trialkylsilyl hydroxyl-protecting group as shown in formula VII.

Treatment of VII with mercuric acetate in acetic acid at a temperature of about 90° C. yields the olefin VIII.

In order to obtain the desired azetidinone IX, the olefin VIII is ozonized in a reaction-inert solvent such as dichloromethane at a temperature of between about −80° and −40° C., preferably about −78° C. The reaction product is treated with an alkanol such as methanol to yield the azetidine IX.

As shown in Scheme B, a compound of formula IX is treated with trithiocarbonate salt of the formula $M^+R_{10}-S-C(S)-S^-$ wherein $R_{10}$ is alkyl having 1-4 carbon atoms, preferrably, ethyl, and M is a metal such as sodium or potassium to obtain a compound of formula X. This conversion of IX to X is carried out in an organic solvent or water, preferably a mixture of water and dichloromethane at a temperature range of about 0°-35° C., preferably about 25° C.

The compound of formula X is condensed with p-nitrobenzyl chloro-oxalate in the presence of a tertiary alkylamine wherein each alkyl has, for example, 1-4 carbon atoms such as ethyl-di-isopropylamine, to obtain the compound of formula XI. This condensation reaction is carried out in a reaction-inert solvent, preferably dichloromethane, at a temperature range of about 5°-25° C., preferably about 10° C.

The resulting compound of formula XI is cyclized using a trialkyl phosphite wherein each alkyl has 1-4 carbon atoms such as triethylphosphite in a reaction-inert solvent such as trichloromethane at a temperature range of about 40°-80° C., preferably about 60° C. to obtain the penem of formula XII.

The thio group of compound XII is oxidized to the corresponding sulfoxide XIII with an oxidizing agent such as m-chloroperbenzoic acid in a reaction inert solvent such as dichloromethane, at a temperature range of about −10° to −30° C., preferably −20° C.

The sulfoxide in the compound of formula XIII is substituted with the mercaptide of formula $R-S^-$ by employing, for example, the sodium or potassium salt of the appropriate mercaptide which is reacted with the sulfoxide XIII in a polar organic solvent such as ethanol or acetonitrile at a temperature range of about −10° to −50° C., preferably about −35° C.

Starting mercaptans of the formula R—SH or starting thioacetates of the formula $R-S-C(O)CH_3$ are known for many of the values of R and those which are not known can be prepared by analogous methods known in the art. For a review see J. L. Wardell, "Preparation of Thiols," in *The Chemistry of the Thiol Group*, S. Patai, editor, John Wiley & Sons, London, 1974, Chapter 4. See also Volante, *Tetrahedron Letters*, 22, 3119-3122(1981) for the conversion of alcohols to thiols and thiolesters using triphenylphosphine and a dialkyl azodicarboxylate in the presence of the alcohol and an appropriate thiolacid.

For compounds of formula XIV the trialkylsilyl group is preferably removed prior to the hydrogenolysis to remove the acid-protecting group (PNB) to obtain a compound of formula XV. The trialkylsilyl group is removed with a tetraalkylammonium fluoride in an ethereal solvent such as tetrahydrofuran at a temperature range of about 15° to 40° C., preferably about 25° C.

Conversion of a compound of formula XV to a compound of formula II is accomplished using a conventional hydrogenolysis reaction, and it is carried out in conventional fashion for this type of transformation. Thus, a solution of a compound of the formula XV is stirred or shaken under an atmosphere of hydrogen, or hydrogen mixed with an inert diluent such as nitrogen or argon, in the presence of a catalytic amount of a noble metal hydrogenolysis catalyst, such as a palladium-on-calcium carbonate or a palladium-on-Celite (a diatomaceous earth) catalyst. Convenient solvents for this hydrogenolysis are lower alkanols, such as methanol; ethers, such as tetrahydrofuran and dioxan; low molecular weight esters, such as ethyl acetate and butyl acetate; water; and mixtures of these solvents. However, it is usual to choose conditions under which the starting material is soluble such as aqueous tetrahydrofuran. The hydrogenolysis is usually carried out at room temperature and at a pressure from about 0.5 to about 5 kg/cm². The catalyst is usually present in an amount from about 10 percent by weight based on the starting material up to an amount equal in weight to the starting material, although larger amounts can be used. The reaction commonly takes about one hour after which the compound of the formula II is recovered simply by filtration followed by removal of the solvent in vacuo. If palladium-on-calcium carbonate is used as the catalyst, the product is isolated as the calcium salt and if palladium-on-Celite is employed the product is isolated as the sodium salt.

The compounds of formula I or II can be purified by conventional methods for beta-lactam compounds. For example, the compound of formula I can be purified by gel filtration on Sephadex, or by recrystallization.

An alternate synthetic procedure is shown in Scheme C. The azetidine of formula IX is reacted with a trithiocarbonate of the formula $M^+R-S-C(S)-S^-$ wherein M is a metal such a sodium or potassium using the procedure previously described to prepare X.

The resulting trithiocarbonate XVA is treated with (p-nitrobenzyloxycarbonyl) (dihydroxy)methane in an aprotic solvent such as benzene, toluene or dimethylformamide, preferably benzene, at a temperature range of about 25°-110° C., preferably about 80° C. to yield the alcohol of formula XVI.

The corresponding chloride XVII is prepared from the alcohol XVI by treatment with thionyl chloride in a reaction-inert organic solvent such as dichloromethane in the presence of a hindered amine which serves as an acid acceptor such as 2,6-lutidine at a temperature range of about −10° to 75° C., preferably 0° C.

The chloride XVII is reacted with a triarylphosphine, such as triphenylphosphine, in a reaction-inert solvent such as tetrahydrofuran in the presence of a tertiary amine, such as 2,6-lutidine, at a temperature of about 25° C., to obtain the compound of formula XVIII which is cyclized by refluxing in an aromatic solvent such as toluene to yield the penem of formula XIV.

Trithiocarbonate salts of the formula $M^+R—S—(C=S)—S^-$ are prepared from the appropriate mercaptan of the formula R—SH or by treatment of a thioacetate of the formula $RSC(O)CH_3$ with an alkaline metal alkoxide followed by carbon disulfide.

By employing the heretofore mentioned procedure of Yoshida et al., the stereochemistry at carbon 6 of the penem as well as the hydroxyethyl group attached to carbon 6 is that shown in formula II. Thus, the principal stereochemistry for the product of ring closure using Schemes B or C is that wherein the hydrogen at penem ring position 5 is trans to the hydrogen on carbon 6 and in the alpha configuration. Alternatively, the stereochemistry can be described as 5R,6S; 6-(R)-1-hydroxyethyl.

The compounds of formula I or II are acidic and will form salts with basic agents. Such salts are considered to be within the scope of this invention. These salts can be prepared by standard techniques, such as contacting the acidic and basic components, usually in a stoichiometric ratio, in an aqueous, non-aqueous or partially aqueous medium, as appropriate. They are then recovered by filtration, by precipitation with a non-solvent followed by filtration, by evaporation of the solvent, or in the case of aqueous solutions by lyophilization, as appropriate. Basic agents which are suitably employed in salt formation belong to both the organic and inorganic types, and they include ammonia, organic amines, alkali metal hydroxides, carbonates, bicarbonates, hydrides and alkoxides, as well as alkaline earth metal hydroxides, carbonates, hydrides and alkoxides. Representative examples of such bases are primary amines, such as n-propylamine, n-butylamine, aniline, cyclohexylamine, benzylamine and octylamine; secondary amines, such as diethylamine, morpholine, pyrrolidine and piperidine; tertiary amines, such as triethylamine, N-ethylpiperidine, N-methylmorpholine and 1,5-diazabicyclo[4,3,0]non-5-ene; hydroxides, such as sodium hydroxide, potassium hydroxide, ammonium hydroxide and barium hydroxide; alkoxides, such as sodium ethoxide and potassium ethoxide; hydrides, such as calcium hydride and sodium hydride; carbonates, such as potassium carbonate and sodium carbonate; bicarbonates, such as sodium bicarbonate and potassium bicarbonate; and alkali metal salts of long-chain fatty acids, such as sodium 2-ethylhexanoate.

Preferred salts of the compounds of formula I or II are sodium, potassium and calcium salts.

The pharmaceutically acceptable salts of formula I or II are those which are free of significant adverse side effects at the level of ordinary use and include, e.g., the sodium, potassium or calcium salts thereof.

The in vitro antibacterial activity of the compounds of formula I or II and salts thereof can be demonstrated by measuring their minimum inhibitory concentrations (MIC's) in mcg/ml against a variety of microorganisms. The procedure which is followed is the one recommended by the International Collaborative Study on Antibiotic Sensitivity Testing (Ericcson and Sherris, *Acta. Pathologica et Microbiologia Scandinav*, Supp. 217, Section B: 64–68 [1971]), and employs brain heart infusion (BHI) agar and the inocula replicating device. Overnight growth tubes are diluted 100-fold for use as the standard inoculum (20,000–10,000 cells in approximately 0.002 ml. are placed on the agar surface; 20 ml. of BHI agar/dish). Twelve 2-fold dilutions of the test compound are employed, with initial concentration of the test drug being 200 mcg/ml. Single colonies are disregarded when reading plates after 18 hrs. at 37° C. The susceptibility (MIC) of the test organism is accepted as the lowest concentration of compound capable of producing complete inhibition of growth as judged by the naked eye.

The compounds of formula I or II, and the pharmaceutically-acceptable salts thereof, are suitable for the control of bacterial infections in mammals, including man. They will find use in the control of infections caused by susceptible bacteria in human subjects, e.g. infections caused by susceptible strains of *Staphylococcus aureus*.

The compounds of the present invention can be administered orally or parenterally, i.e. intramuscularly, subcutaneously, intraperitoneally or intravenously, alone, or combined with a pharmaceutically-acceptable carrier according to standard pharmaceutical practice. The ratio of active ingredient to carrier will depend upon the chemical nature, solubility and stability of the active ingredient, as well as the dosage contemplated. The ratio of the pharmaceutically-acceptable carrier to the penem compound will normally be in the range from 1:10 to 4:1. For the oral administration, the compounds of this invention can be used in the form of tablets, capsules, lozenges, troches, powders, syrups, elixirs, aqueous solutions and suspensions, and the like. In the case of tablets, carriers which can be used include lactose, sodium citrate and salts of phosphoric acid. Various disintegrants such as starch, and lubricating agents, such as magnesium stearate, sodium lauryl sulfate and talc, are commonly used in tablets. Useful diluents for capsules include lactose and high molecular weight polyethylene glycols. When aqueous suspensions are required for oral use, the active ingredient is combined with emulsifying and suspending agents. Sweetening and/or flavoring agents can be added. For parenteral administration, sterile solutions of the active ingredient are usually prepared, and the pH of the solutions are suitably adjusted and buffered. For intravenous use, the total concentration of solutes should be controlled to render the preparation isotonic. The prescribing physician will ultimately determine the appropriate dose for a given human subject, and this can be expected to vary according to the age, weight, and response of the individual patient, as well as the nature and the severity of the patient's symptoms. The compounds of formula I or II will normally be used orally at dosages in the range from about 10 to about 200 mg. per kilogram of body weight per day, and parenterally at dosages from about 10 to about 400 mg. per kilogram of body weight per day. In some cases it may be necessary to use dosages outside these limits.

The following Examples and Preparations are provided solely for further illustration. Infra-red (IR) spectra were measured either as potassium bromide discs (KBr disc), Nujol mulls or as solutions in chloroform ($CHCl_3$), methylene chloride ($CH_2Cl_2$) or dimethyl sulfoxide (DMSO), and diagnostic absorption bands are reported in either microns or wave numbers ($cm^{-1}$). Nuclear magnetic resonance (NMR) spectra were measured for solutions in deuterochloroform ($CDCl_3$), perdeuteromethanol ($CD_3OD$) or perdeuterodimethyl sulfoxide (DMSO-$d_6$), or mixtures thereof, and peak positions are expressed in parts per million downfield from tetramethylsilane. The following abbreviations for peak shapes are used: s, singlet; d, doublet; t, triplet; q, quartet; m, multiplet; b, broad; c, complex. The abbreviations "ss" and "sss" denote that a particular proton appeared as two or three singlets respectively, owing to the presence of diastereoisomers. Throughout the Examples and Preparations, the abbreviation "PNB" represents the p-nitrobenzyl group.

EXAMPLE 1

Sodium (5R,6S)-6-[(R)-1-Hydroxyethyl]-2-(2-pyrrolidon-3-yl)thio-2-penem-3-carboxylate The pH of a suspension of 73 mg. 10% Pd on diatomaceous earth in a mixture of 20 ml. tetrahydrofuran and 20 ml. distilled water was adjusted to 8.3 with 0.02M aqueous sodium bicarbonate solution. A solution of 73 mg. p-nitrobenzyl (5R,6S)-6-[(R)-1-hydroxyethyl]-2-(2-pyrrolidon-3-yl)thio-2-penem-3-carboxylate in a mixture of 8 ml. tetrahydrofuran and 8 ml. water was then added and the resulting mixture was hydrogenated at 55 p.s.i. of hydrogen for 75 min.; 73 mg. more of 10% Pd on diatomaceous earth was then added and the pH of the mixture was adjusted to 7.0 with 0.02M aqueous sodium bicarbonate solution. The mixture was hydrogenated at 55 p.s.i. for 75 min.; then the catalyst was removed by filtration and the filtrate was concentrated in vacuo to remove tetrahydrofuran. The pH of the resulting aqueous solution was adjusted to 7.0 and the solution extracted with two 15 ml. portions of ethyl acetate. The aqueous solution was then lyophilized, yielding 38 mg. (69% yield) of the title compound as an amorphous solid.

The infrared spectrum of the title compound as a potassium bromide disc had absorptions at 2.94, 5.65 and 6.3 microns.

EXAMPLE 2

The procedures of Example 1 were employed using appropriate compounds of formula XV to obtain the sodium salts of compounds of formula II whose yield, potassium bromide disc (unless otherwise indicated) infrared spectrum and R are as shown in Table 1.

TABLE 1

| R | IR(microns) | Yield (%) |
|---|---|---|
| 2-pyrrolidon-4-yl | 2.92, 5.68, 6.0 and 6.15 | 88 |
| 1-formyl-3-pyrrolidinyl | 2.92, 5.64, 6.03 and 6.3 | 89 |
| (3-methyl-1,3-oxazolidin-2-on-5-yl)methyl | 2.94, 5.7 and 6.25 | 78 |
| (3-methyl-1,3-oxazolidin-2-on-4-yl)methyl | 2.94, 5.7 and 6.28 | 90 |
| 2-piperidon-5-yl | 5.64, 6.02 and 6.3 (DMSO) | 93 |
| piperidin-2-on-3-yl | 2.94, 5.66, 6.06 and 6.25 | 79 |
| 1-methylpiperidin-2-on-3-yl | 2.93, 5.64 and 6.15 | 98 |
| 1-formylpiperidin-3-yl | 2.9, 5.65 and 6.03 | 73 |
| 3-methyl-perhydro-1,3-oxazin-2-on-5-yl (from less soluble diastereomer) | 2.92, 5.63, 5.99 and 6.08 | 57 |
| 3-methyl-perhydro-1,3-oxazin-2-on-5-yl (from more soluble diastereomer) | 5.65 (DMSO) | 84 |

EXAMPLE 3

Sodium (5R,6S)-6-[(R)-1-Hydroxyethyl]-2-(pyrrolidin-2,5-dion-3-yl)thio-2-penem-3-carboxylate The procedures of Example 1 were employed except the initial pH was 7.5 and for the starting compound of formula XV, R was pyrrolidin-2,5-dion-3-yl. The compound was obtained in 90% yield and had infrared spectrum absorptions, as a potassium bromide disc, at 2.92, 5.63, 5.8 and 6.2 microns.

EXAMPLE 4

The procedures of Example 3 were employed using appropriate compounds of formula XV to obtain the sodium salts of compounds of formula II whose yield, potassium bromide disc (unless otherwise indicated) infrared spectrum and R are as shown in Table 1A.

TABLE 1A

| R | IR(microns) | Yield (%) |
|---|---|---|
| (1,3-oxazolidin-2-on-4-yl)methyl | 5.72(b) | 95 |
| (1,3-oxazolidin-2-on-5-yl)methyl | 5.72(b) | 87 |
| (1,3-thiazolidin-2-on-4-yl)methyl | 5.65 | 100 |

PREPARATION A p-Nitrobenzyl(5R,6S)-6-[(R)-1-Hydroxyethyl]-2-(2-pyrrolidon-3-yl)thio-2-penem-3-carboxylate To a solution of 118 mg. (0.204 mmole) p-nitrobenzyl (5R,6S)-6-[(R)-1-t-butyldimethylsilyloxyethyl]-2-(2-pyrrolidon-3-yl)thio-2-penem-3-carboxylate in 6 ml. tetrahydrofuran was added 0.11 ml (2.04 mmoles) acetic acid and 0.612 ml. (0.612 mole) of a 1M solution of tetrabutylammonium fluoride in tetrahydrofuran. After stirring for 20 hours under nitrogen at room temperature, 50 ml. ethyl acetate was added and the resulting solution was washed with 40 ml. saturated aqueous sodium bicarbonate solution, 40 ml. water and 40 ml. saturated aqueous sodium chloride solution. The ethyl acetate layer was dried over anhydrous sodium sulfate and concentrated in vacuo. The crude product (110 mg.) was chromatographed on silica gel (50 g.), eluting with 95:5 ethyl acetate methanol, to yield 73 mg. (77% yield) of the title compound as an amorphous solid.

The NMR spectrum of a deuterochloroform solution of the title compound had peaks at 1.32(d, 3H); 2.0–3.2 (c, 3H); 3.2–4.37(c, 5H); 5.3(q, 2H); 5.6(d, 1H); 6.64(b, 1H); 7.6(d, 2H); and 8.2(d, 2H) ppm. The infrared spectrum of a dichloromethane solution of the title compound had absorption at 5.58, 5.85 and 6.57 microns.

PREPARATION B

The procedures of Preparation A were employed using compounds of formula XIV to obtain compounds of formula XV whose properties and R are as shown in Table 2. The solvents in which the spectrum were measured are in parentheses.

TABLE 2

| R | IR(microns) | NMR(ppm) | Yield (%) |
|---|---|---|---|
| 2-pyrrolidon-4-yl | 5.58, 5.87 and 6.58 (CH$_2$Cl$_2$) | 1.3(d, 3H); 2.0–4.42(c, 8H); 5.3 (q, 2H); | 87 |

TABLE 2-continued

| R | IR(microns) | NMR(ppm) | Yield (%) |
|---|---|---|---|
| | | 5.68 (d, 1H); 6.25 (b, 1H); 7.56 (d, 2H); and 8.18 (d, 2h). (CDCl$_3$) | |
| 1-formyl-3-pyrrolidinyl | 5.57, 5.96 and 6.56 (CH$_2$Cl$_2$) | 1.35(d,3H); 1.8–2.6(c,2H); 3.2 (b,1H); 3.3–4.46 (c,7H); 5.3(q,2H); 5.64(d,1H); 7.6 (d,2H); and 8.2 (s and d, 3H); (CDCl$_3$) | 42 |
| (3-methyl-1,3-oxazolidin-2-on-5-yl)methyl | 5.56, 5.66 and 6.57 (CH$_2$Cl$_2$) | 1.36 (d,3H); 2.4 (b,1H); 2.9 (s, 3H); 3.17–3.92 (c, 5H); 4.0–4.86 (c, 2H) 5.31 (q,2H); 5.69 (d, 1H); 7.6 (d, 2H); and 8.2 (d, 2H). (CDCl$_3$) | 38 |
| (3-methyl-1,3-oxazolidin-2-on-4-yl)methyl | 5.56, 5.67 and 6.56 (CH$_2$Cl$_2$) | 1.35 (d, 3H); 2.2 (b,1H); 2.89 (s) and 2.81–3.5 (c), (total 5H); 3.6–4.49 (c, 5H); 5.3 (q, 2H); 5.67 (d, 1H); 7.56 (d, 2H); and 8.16 (d, 2H). (CDCl$_3$) | 25 |
| pyrrolidin-2,5-dion-3-yl | 5.57, 5.75 and 6.54 (CH$_2$Cl$_2$) | 1.3 (d, 3H); 2.1 (b,1H); 2.5–4.4 (c,6H); 5.3 (q, 2H); 5.65 (d,1H); 7.56 (d, 2H); and 8.16 (d, 2H). (CDCl$_3$) | 32 |
| 2-piperidon-5-yl | 5.64 and 6.0 (Nujol mull) | 1.18 (d, 3H); 1.74–2.8 (c, 4H); 3.05–3.74 (c, 4H); 4.03 (m, 1H); 5.25 (d, 1H); 5.37 (q, 2H); 5.78 (d, 1H); 7.66 (b, 1H); 7.7 (d, 2H); and 8.25 (d, 2H). (DMSO-d$_6$, 250MHz) | 86 |
| (1,3-oxazolidin-2-on-4-yl)methyl | 5.5, 5.67, 5.91 and 6.58 (CH$_2$Cl$_2$) | 2.0 (b, 1H); 1.27 (d, 3H); 3.1 (m, 2H); 3.7 (dd, 1H); 3.8–4.67 (c, 4H); 5.31 (q, 2H); 5.68 (d, 1H); 7.1 (b, 1H); 7.6 (d, 2H); and 8.18 (d, 2H). (CDCl$_3$/CD$_3$OD) | 57 |
| (1,3-oxazolidin-2-on-5-yl)methyl | 5.58, 5.67 and 6.58 (CH$_2$Cl$_2$) | 1.29 (d, 3H); 2.2 (b, 1H); 3.1–3.98 (C, 5H); 4.1 (m, 1H); 4.83 (C, 2H); 5.3 (q, 2H); 5.7 (d, 1H); 7.1 (b, 1H); 7.58 (d, 2H); and 8.17 (d, 2H). (CDCl$_3$/DMSO-d$_6$) | 56 |
| (1,3-thiazolidin-2-on-4-yl)methyl | 5.61, 5.97, 6.06, 6.6 and 6.7 (KBr) | 1.18 (d, 3H); 3.13–3.46 (C, 3H); 3.62 (dd, 1H); 3.88 (dd, 1H); 4.02 (m, 1H); 4.1 (m, 1H); 5.25 (d, 1H); 5.38 (q, 2H); 5.76 (d, 1H); 7.7 (d, 2H); 8.24 (d, 2H); and 8.42 (s, 1H). | 64 |
| piperidin-2-on-3-yl | 5.56, 5.9, 6.0 and 6.56 (CH$_2$Cl$_2$) | (250 MHz, DMSO-d$_6$) 1.3 (d, 3H); 1.65–2.45 (c, 4H); 3.28 (c, 2H); 3.52–4.42 (c, 4H); 5.32 (q, 2H); 5.65 and 5.7 (2d, total 1H); 7.12 (b, 1H); 7.6 (d, 2H); and 8.2 (d, 2H). (CDCl$_3$/DMSO-d$_6$) | 65 |
| 1-methylpiperidin-2-on-3-yl | 5.56, 5.92, 6.07 and 6.56 (CH$_2$Cl$_2$) | 1.3 (d, 3H); 1.7–2.45 (c, 5H); 2.96 (s, 3H); 3.3 (m, 2H); 3.65–4.45 (c, 3H); 5.3 (q, 2H); 5.6 (d, 1H); 7.57 (d, 2H); and 8.2 (d, 2H). (CDCl$_3$) | 40 |
| 1-formylpiperidin-3-yl | 5.57, 5.97 and 6.56 (CH$_2$Cl$_2$) | 1.12–2.33 (c) and 1.3 (d) (total 8H); 2.78–4.62 (c, 7H); 5.28 (q, 2H); 5.63 (d, 1H); 7.54 (d, 2H); 7.98 (s, 1H); and 8.16 (2H). (CDCl$_3$) | 64 |

PREPARATION C p-Nitrobenzyl (5R,6S)-6-[(R)-1-Hydroxyethyl]-2-(3-methylperhydro-1,3-oxazin-2-on-5-yl)thio-2-penem-3-carboxylate Tetrabutylammonium fluoride (1.25 ml. of a 1M solution in tetrahydrofuran, 1.25 mmole) and acetic acid (0.25 ml) were added to a solution of p-nitrobenzyl (5R,6S)-6-[(R)-1-t-butyldimethylsilyloxyethyl]-2-(3-methyl-perhydro-1,3-oxazin-2-on-5-yl)thio-2-penem-3-carboxylate (0.24 g., 0.39 mmole) in 2 ml. anhydrous tetrahydrofuran. The resulting solution was stirred at 25° C. under nitrogen for 20 hours. The reaction solution was then diluted with 100 ml. ethyl acetate and washed with 10 ml. water, two 20 ml. portions of brine, 20 ml. water and 20 ml. brine, dried over anhydrous sodium sulfate and concentrated in vacuo. The residual solid was triturated with 5 ml. methanol, then 15 ml. diethyl ether was added and the resulting mixture was filtered to yield 71 mg. of the less soluble diastereomer as a light tan colored solid. The filtrate was concentrated in vacuo and the residue was chromatographed on silica gel (75 g.), eluting with 9:1 ethyl acetate-methanol to yield the more soluble diastereomer as a solid. Trituration of the solid with 1:1 diethyl ether-petroleum ether and filtration yielded 52 mg. of the more soluble diastereomer as a light tan colored solid. (Total yield 63%).

less soluble diastereomer
 NMR(DMSO-d$_6$, 250 MHz): 1.2 (d, 3H), 2.86 (s, 3H); 3.4 (dd, 1H); 3.83 (dd, 1H); 3.9–4.1 (c, 3H); 4.25 (dd, 1H); 4.51 (dd, 1H); 5.26 (d, 1H); 5.38 (q, 2H); 5.8 (d, 1H); 7.7 (d, 2H); and 8.26 (d, 2H) ppm.

more soluble diastereomer
 NMR(DMSO-d$_6$, 250 MHz): 1.2 (d, 3H); 2.86 (s, 3H); 3.35 (dd, 1H); 3.81 (dd, 1H); 3.9–4.1 (c, 3H); 4.29 (dd, 1H); 4.54 (dd, 1H); 5.26 (d, 1H); 5.39 (q, 2H); 5.83 (d, 1H); 7.7 (d, 2H); and 8.26 (d, 2H) ppm. IR (KBr); 2.92, 5.61, 5.85, 5.91 and 6.61 microns.

PREPARATION D p-Nitrobenzyl(5R,6S)-6-[(R)-1-t-Butyldimethylsilyloxyethyl]-2-(2-pyrrolidon-3-yl)thio-2-penem-3-carboxylate Sodium methoxide (27 mg., 0.5 mmole) was added to a solution of 80 mg. (0.5 mmole) 2-pyrrolidon-3-yl thioacetate in 5 ml. anhydrous ethanol cooled to −30° C. under nitrogen. After 30 minutes at −30° C., a solution of 300 mg. (0.5 mmole) crude p-nitrobenzyl(5R,6S)-6-[(R)-1-t-butyldimethylsilyloxyethyl]-2-ethylsulfinyl-2-penem-3-carboxylate of Preparation I in 5 ml. anhydrous tetrahydrofuran which had been cooled to −50° C., was added. The resulting solution was stirred at −30° C. for 60 minutes, then 0.029 ml. (0.5 mmole) acetic acid was added and the solution was concentrated in vacuo. The residue was dissolved in 50 ml. ethyl acetate and the resulting solution was washed with 40 ml. saturated aqueous sodium bicarbonate solution, 40 ml. water and 40 ml. saturated aqueous sodium chloride solution. The ethyl acetate layer was dried over anhydrous sodium sulfate and concentrated in vacuo. Chromatography of the crude product (370 mg.) on silica gel (120 g.), eluting with 1:1 chloroform/ethyl acetate yielded 118 mg. (41% yield) of the title compound as a viscous gum.

The infrared spectrum of a dichloromethane solution of the title compound had absorptions at 5.58, 5.86 and 6.58 microns. The NMR spectrum of deuterochloroform solution of the title compound had peaks at 0.06(s, 3H); 0.1(s, 3H); 0.84 (s, 9H); 1.24(d, 3H); 1.92–2.98 (c, 2H); 3.23–4.4 (c, 5H); 5.29 (q, 2H); 5.6(d, 1H); 6.6 (b, 1H); 7.55 (d, 2H); and 8.16 (d, 2H) ppm.

PREPARATION E

The procedures of Preparation D were employed using the appropriate thioacetate to obtain compounds of formula XIV whose properties and R are as shown in Table 3.

TABLE 3

| R | IR(microns) | NMR(ppm) | Yield (%) |
|---|---|---|---|
| 2-pyrrolidon-4-yl | 5.58, 5.86 and 6.57 (CH₂Cl₂) | 0.04 (s, 3H); 0.09 (s, 3H); 0.82 (s, 9H); 1.25 (d, 3H); 2.1–4.42 (c, 7H); 5.29 (q, 2H); 5.62 (d, 1H); 6.44 (b, 1H); 7.57 (d, 2H); and 8.16 (d, 2H). (CDCl₂) | 31 |
| 1-formyl-3-pyrrolidinyl | 5.58, 6.02 and 6.57 (CH₂Cl₂) | 0.02 (s, 3H); 0.09 (s, 3H); 0.85 (s, 9H); 1.24 (d, 3H); 0.08–2.42 (c, 2H); 3.3–4.47 (c, 7H); 5.28 (q, 2H); 5.64 (d, 1H); 7.55 (d, 2H); and 8.16 (d) and 8.18 (s), (total 3H). (CDCl₃) | 37 |
| (3-methyl-1,3-oxazolidin-2-on-5-yl)methyl | 5.57, 5.66 5.9 and 6.57 (CH₂Cl₂) | 0.05 (s, 3H); 0.1 (s, 3H); 0.85 (s, 9H); 1.26 (d, 3H); 2.89 (s, 3H); 3.12–3.89 (c, 5H); 4.04–4.8 (c, 2H); 5.3 (q, 2H); 5.67 (d, 1H); 7.6 (d, 2H); and 8.2 (d, 2H). (CDCl₃) | |
| (3-methyl-1,3-oxazolidin-2-on-4-yl)methyl | 5.56, 5.67, 5.88 and 6.57 (CH₂Cl₂) | 0.02 (s, 3H); 0.08 (s, 3H); 0.82 (s, 9H); 1.26 (d, 3H); 2.9 (s) and 2.8–3.5 (c), (total 5H); 3.65–4.54 (c, 5H); 5.3 (q, 2H); 5.69 (d, 1H); 7.6 (d, 2H); and 8.2 (d, 2H). (CDCl₃) | 48 |
| 2-piperidon-5-yl | 5.62 and 6.0 (Nujol mull) | 0.04 (s, 3H); 0.08 (s, 3H); 0.84 (s, 9H); 1.27 (d, 3H); 1.85–2.7 (c, 4H); 3.34–3.84 (c, 4H); 4.28 (m, 1H); 5.33 (q, 2H); 5.69 (d, 1H); 6.06 (b, 1H); 7.63 (d, 2H); and 8.22 (d, 2H). (CDCl₃, 250 MHz) | 34 |
| piperidin-2-on-3-yl | 5.57, 5.98 and 6.56 (CH₂Cl₂) | 0.03 (s, 3H); 0.06 (s, 3H); 0.84 (s, 9H); 1.22 (d, 3H); 1.66–2.4 (c, 4H); 3.34 (c, 2H); 3.6–4.5 (c, 3H); 5.26 (q, 2H); 5.56 and 5.62 (2d, total 1H); 6.5 (b, 1H); 7.54 (d, 2H); and 8.14 (d, 2H). (CDCl₃) | 29 |
| 1-methylpiperidin-2-on-3-yl | 5.57, 5.93, 6.08 and 6.56 (CH₂Cl₂) | 0.03 (s, 3H); 0.06 (s, 3H); 0.82 (s, 9H); 1.22 (d, 3H); 1.6–2.36 (c, 4H); 2.96 (s, 3H); 3.3 (m, 2H); 3.67–4.43 (c, 3H); 5.28 (q, 2H); 5.57 (d, 1H); 7.57 (d, 2H); and 8.18 (d, 2H). (CDCl₃) | 40 |
| 1-formylpiperidin-3-yl | 5.58, 5.98, 6.58 (CH₂Cl₂) | 0.03 (s, 3H); 0.06 (s, 3H); 0.82 (s, 9H); 1.1–2.3 (c) and 1.23 (d) (total 7H); 2.8–4.5 (c, 7H); 5.26 (q, 2H); 5.62 (d, 1H); 7.54 (d, 2H); 7.98 (s, 1H); and 8.14 (d, 2H). (CDCl₃) | 48 |

PREPARATION F

The procedures of Preparation D were employed using purified p-nitrobenzyl(5R,6S)-6-[(R)-1-t-butyldimethylsilyloxyethyl]-2-ethylsulfinyl-2-penem-3-carboxylate of Preparation H and the appropriate thioacetate to obtain compounds of formula XIV whose properties and R are as shown in Table 3A.

TABLE 3A

| R | IR(microns) | NMR(ppm) | (Yield (%)) |
|---|---|---|---|
| (1,3-oxazolidin-2-on-4-yl)methyl | 5.57, 5.67, 5.92 and 6.58 (CH$_2$Cl$_2$) | 0.03 (s, 3H); 0.06 (s, 3H); 0.82 (s, 9H); 1.22 (d, 3H); 3.1 (2d, 2H); 3.72 (dd, 1H); 3.82–4.68 (c, 4H); 5.26 (q, 2H); 5.64 (d, 1H); 5.98 (b, 1H); 7.54 (d, 2H), and 8.16 (d, 2H). (CDCl$_3$) | 40 |
| (1,3-oxazolidin-2-on-5-yl)methyl | 5.6, 5.67, 5.92 and 6.58 (CH$_2$Cl$_2$) | 0.03 (s,3H); 0.06 (s, 3H); 0.82 (s, 9H); 1.22 (d, 3H); 3.1–4.0 (c, 5H); 4.22 (m, 1H); 4.8 (m, 1H); 5.29 (q, 2H); 5.65 (d, 1H); 5.84 (b, 1H); 7.56 (d, 2H); and 8.16 (d, 2H). (CDCl$_3$) | 48 |
| (1,3-thiazolidin-2-on-4-yl)methyl | 5.56, 5.89 and 6.54 (CH$_2$Cl$_2$) | 0.03 (s, 3H); 0.06 (s, 3H); 0.82 (s, 9H); 1.22 (d, 3H); 3.0–4.42 (c, 7H); 5.3 (q, 2H); 5.66 (d, 1H); 6.0 (b, 1H); 7.56 (d, 2H); and 8.16 (d, 2H). (CDCl$_3$) | 50 |
| 3-methyl-perhydro-1,3-oxazin-2-on-5-yl-methyl | | 0.05 (s, 3H); 0.08 (s, 3H); 0.84 (s, 9H); 1.27 (d, 3H); 3.0 (s, 3H); 3.37 (dd, 1H); 3.67 (dd, 1H); 3.8 (c, 2H); 4.14–4.34 (c, 2H); 4.47 (dd, 1H); 5.33 (q, 2H); 5.72 (d, 1H); 7.62 (d, 2H); and 8.23 (d, 2H). (CDCl$_3$, 250 MHz) | 82 |

PREPARATION G p-Nitrobenzyl(5R,6S)-6-[(R)-1-t-Butyldimethylsilyloxyethyl]-2-(pyrrolidin-2,5-dion-3-yl)thio-2-penem-3-carboxylate Sodium methoxide (54 mg., 1.0 mmole) was added to a solution of 87 mg. (0.5 mmole) pyrrolidin-2,5-dion-3-yl thioacetate in 5 ml. anhydrous ethanol cooled to −35° C. under nitrogen. After 40 minutes at −35° C., a solution of 300 mg. (ca. 0.5 mmole) crude p-nitrobenzyl(5R,6S)-6-[(R)-1-t-butyldimethylsilyloxyethyl]-2-ethylsulfinyl-2-penem-3-carboxylate in 5 ml. anhydrous tetrahydrofuran which had been cooled to −50° C., was added. The resulting solution was stirred at −40° C. to −35° C. for 60 minutes, 0.058 ml. (1.0 mmole) acetic acid was added and the solution was concentrated in vacuo. The residue was dissolved in 50 ml. ethyl acetate and the resulting solution was washed with 40 ml. saturated aqueous sodium bicarbonate solution, 40 ml. water and 40 ml. saturated aqueous sodium chloride solution. The ethyl acetate layer was dried over anhydrous sodium sulfate and concentrated in vacuo. Chromatography of the crude product (360 mg.) on silica gel (120 g.), eluting with 3:1 chloroform-ethyl acetate, yielded 123 mg. (42% yield) of the title compound as a viscous gum.

The infrared spectrum of the title compound in a dichloromethane solution had absorptions at 5.56, 5.72 and 6.5 microns. The NMR spectrum of a deuterochloroform solution of the title compound had peaks at 0.04 (s, 3H); 0.08 (s, 3H); 0.86 (s, 9H); 1.25 (d, 3H); 2.54–4.54 (c, 5H); 5.3 (q, 2H); 5.7 (d, 1H); 7.6 (d, 2H) and 8.2 (d, 2H) ppm.

PREPARATION H

Purification of p-Nitrobenzyl(5R,6S)-6-[(R)-1-t-Butyldimethylsiloxyethyl]-2-ethylsulfinyl-2-penem-3-carboxylate 8.0 g of the title penem sulfoxide prepared according to Preparation I was chromatographed on silica gel (500 g). Elution with hexane-ethyl acetate (1:1) yielded 4.6 g. of purified title compound as a mixture of diastereomers.

PREPARATION I p-Nitrobenzyl(5R,6S)-6-[(R)-1-t-Butyldimethylsilyloxyethyl]-2-ethylsulfinyl-2-penem-3-carboxylate A solution of 970 mg. (4.78 mmoles, 85% purity) m-chloroperbenzoic acid in 25 ml. methylene chloride was added to a solution of 2.5 g. (4.78 mmoles) of p-nitrobenzyl(5R,6S)-6-[(R)-1-t-butyldimethylsilyloxyethyl]-2-ethylthio-2-penem-3-carboxylate in 125 ml. methylene chloride cooled to −20° C. under a nitrogen atmosphere. The mixture was stirred at −20° C. for 3 hr., then washed sequentially with two 70 ml. portions of saturated aqueous sodium bicarbonate solution, 70 ml. water and 70 ml. saturated aqueous sodium chloride solution. The methylene chloride solution was dried with anhydrous sodium sulfate and concentrated in vacuo to a yellow foam of the title compound (2.2 g., 86% yield).

The infrared spectrum of the title compounds as a dichloromethane solution had absorptions at 5.54, 5.86 and 6.53 microns. The NMR spectrum of the title compound as a deuterochloroform solution had peaks at 0.06, 0.08, 0.1 and 0.12 (4s, total 6H); 0.8(s, 9H); 1.12–1.58 (m, 6H); 3.1 (m, 2H); 3.86(m, 1H), 4.3(m, 1H), 5.3 (m, 2H); 5.67 and 5.78 (2d, total 1H); 7.54(d, 2H); and 8.18 (d, 2H)ppm.

PREPARATION J p-Nitrobenzyl(5R,6S)-6-[(R)-1-t-Butyldimethylsilyloxyethyl]-2-ethylthio-2-penem-3-carboxylate p-Nitrobenzyl oxalyl chloride (5.85 g. 0.024 mole) was added to a mixture of 7.3 g (0.01 mole) (3-alpha-t-butyldimethylsilyloxyethyl-4-ethylthio(thiocarbonyl)thio-2-oxo-azetidine and 4.8 g. (0.048 mole) calcium carbonate in 70 ml. methylene chloride cooled to 10° C. under a nitrogen atmosphere. A solution of 4.17 ml. (0.024) mole) diisopropylethylamine in 20 ml. methylene chloride was added dropwise at a rate to keep the temperature below 12° C. The mixture was stirred for 60 min. at 10° C., then washed with two 50 ml. portions of ice cold water, dried over anhydrous sodium sulfate and concentrated in vacuo to a viscous oil. The resulting crude p-nitrobenzyl(3-alpha-t-butyldimethylsilyloxyethyl-2-oxo-azetidinyl)oxoacetate was dissolved in 300 ml. ethanol-free chloroform and the resulting solution was refluxed under nitrogen while a solution of 6.85 ml. (0.04 mole) triethylphosphite in 50 ml. ethanol-free chloroform was added dropwise over 2 hr. The resulting solution was refluxed for 16 hr., then concentrated in vacuo. The residue was chromatographed on silica gel (800 g.), eluting with 95:5 toluene-ethyl acetate to yield 5.5 g. (53% yield) of the title compound as a yellow foam.

The infrared spectrum of the title compound as a dichloromethane solution had absorptions at 5.56, 5.89 and 6.54 microns. The NMR spectrum of the title compound as a dueterochloroform solution had peaks at 0.07(s, 3H); 0.1(s, 3H); 0.85(s, 9H); 1.12–1.53(m, 6H); 2.97(q, 2H); 3.7(m, 1H); 4.25(m, 1H); 5.3(q, 2H); 5.63(d, 1H); 7.38(d, 2H); and 8.18(d, 2H)ppm.

The NMR spectrum of the intermediate (1-azetidinyl-)oxoacetate as a deuterochloroform solution had peaks at 0.06(s, 6H); 0.8(s, 9H); 1.14–1.62(m, 6H); 3.14–3.63(m, 3H); 4.33(m, 1H); 5.16(s, 2H); 6.7(d, 1H); 7.5(d, 2H); and 8.17(d, 2H)ppm.

PREPARATION K 3-alpha-t-Butyldimethylsilyloxyethyl-4-ethylthio(thiocarbonyl)thio-2-oxo-azetidine Ethanethiol (8.5 ml. 0.115 mole) was added to a solution of 4.18 g. (0.104 mole) sodium hydroxide in 250 ml. water cooled to 0°–5° C. under a nitrogen atmosphere. After 15 min. 7.73 ml. (0.12 mole) carbon disulfide was added and the mixture was stirred at 0°–5° C. for 35 min. A solution of 15.0 g. (0.0522 mole) 4-acetoxy-3-t-butyldimethylsilyloxyethyl-2-azetidinone in 500 ml. methylene chloride was added and the mixture was stirred vigorously at room temperature for 24 hr. The aqueous phase was separated and extracted with two 150 ml. portions of methylene chloride. The combined methylene chloride fractions were washed with two 200 ml. portions of water and 200 ml. saturated aqueous sodium chloride solution, dried over anhydrous sodium sulfate and concentrated in vacuo. The crude title product (18 g.) was chromatographed on silica gel (500 g.), eluting with 99:1 chloroform-ethyl acetate to yield 9.1 g. (48% yield) of title trithiocarbonate as a yellow foam.

The infrared spectrum of the title compound in dichloromethane solution had absorptions at 5.62 and 9.2 microns. The NMR spectrum of a deuterochloroform solution of the title compound had peaks at 0.08(s, 6H); 0.8(s, 9H); 1.02–1.5(m, 6H); 3.0–3.48(m, 3H); 4.12(m, 1H); 5.54(d, 1H); and 6.57(b, 1H)ppm.

PREPARATION L

2-Pyrrolidon-3-yl p-Toluenesulfonate

To a solution of 1.0 g (0.01 mole) 3-hydroxy-2-pyrrolidone in 50 ml. methylene chloride cooled to 0° under nitrogen was added 2.44 g (0.02 mole) 4-dimethylaminopyridine, then 1.9 g (0.01 mole) p-toluenesulfonyl chloride. The resulting solution was stirred at 0° for 30 min., then at room temperature overnight. The solution washed with 50 ml. 1N aqueous hydrochloric acid solution, 50 ml. water and 50 ml. saturated aqueous sodium chloride solution, dried over anhydrous sodium sulfate and concentrated in vacuo to an amorphous solid (2.1 g., 83% yield) of the title compound.

The NMR spectrum of a deuterochloroform solution of the title compound had peaks at 2.44(s) and 1.83–2.64(c) (total 5H); 3.1–3.44 (m, 2H); 4.86 (t, 1H); 7.33 (d, 2H); and 7.8 (d+b, 3H)ppm.

PREPARATION M

The procedures of Preparation L were employed with 1-formyl-3-hydroxypyrrolidine as the starting material to obtain 1-formyl-3-pyrrolidinyl p-toluenesulfonate in 82% yield. The NMR spectrum of a deuterochloroform solution of the product had peaks at 1.9–2.3(c, 2H); 2.46(s, 3H); 3.36–3.78(c, 4H); 5.1(c, 1H); 7.32(d, 2H); 7.778d, 2H); and 8.13(d, 1H)ppm.

In like manner, 3-methyl-perhydro-1,3-oxazin-2-on-5-yl p-toluenesulfonate was prepared from the corresponding alcohol (81%). The NMR spectrum of a deuterochloroform solution had peaks at 2.44 (S, 3H); 2.9 (s, 3H); 3.46 (m, 2H): 4.18 (m, 2H); 4.9 (m, 1H); 7.3 (d, 2H); and 7.74 (d, 2H) ppm.

PREPARATION N

2-Pyrrolidon-4-yl p-Toluenesulfonate

To a solution of 0.71 g. (7.02 mmole) 4-hydroxy-2-pyrrolidone in 35 ml. methylene chloride cooled to 0° C. under nitrogen was added 1.72 g (14.04 mole) 4-dimethylaminopyridine, followed by 1.34 g. (7.02 mmole) p-toluensulfonyl chloride. The resulting solution was allowed to warm to room temperature and was stirred for 3 hr. The solution was then washed with 2×30 ml. 1N aqueous hydrochloric acid solution, 30 ml. saturated aqueous sodium bicarbonate solution and 30 ml. saturated aqueous sodium chloride solution, dried over anhydrous sodium sulfate and concentrated in vacuo to an amorphous solid (1.5 g., 84% yield) of the title compound.

The NMR spectrum of deuterochloroform solution of the title compound had peaks at 2.46(s) and 2.02–2.84(c) (total 5H); 3.24–3.86(c, 2H); 5.17(c, 1H); 7.1(b, 1H); 7.34(d, 2H); and 7.76(d, 2H)ppm.

PREPARATION O

The procedures of Preparation N were employed using 5-hydroxymethyl-3-methyl-1,3-oxazolidin-2-one as the starting alcohol to obtain (3-methyl-1,3-oxazolidin-2-on-5-yl)methyl p-toluenesulfonate in 85% yield whose NMR spectrum as a deuterochloroform solution had peaks at 2.44 (s, 3H); 2.82 (s, 3H); 3.16–3.8(m, 2H); 4.12(d, 2H); 4.66(c, 1H); 7.33(d, 2H); and 7.74(d, 2H)ppm. Likewise, with 4-hydroxymethyl-3-methyl-1,3-oxazolidin-2-one as the starting alcohol, (3-methyl-1,3-oxazolidin-2-on-4-yl)methyl p-toluenesulfonate was obtained in 88% yield having an NMR spectrum as a deuterochloroform solution with peaks at 2.45 (s, 3H); 2.77 (s, 3H); 3.66–4.52 (c, 5H); 7.32 (d, 2H); and 7.74 (d, 2H)ppm.

In like manner 1-formylpiperidin-3-yl p-toluenesulfonate was prepared from the corresponding alcohol in 75% yield. NMR (CDCl$_3$): 1.22–2.17 (C, 4H); 2.46 (s, 3H); 2.96–3.9 (c, 4H); 4.53 (m, 1H); 7.34 (d, 2H); 7.8 (d, 2H); 7.93 (d, 1H).

PREPARATION P

2-Pyrrolidon-3-yl Thioacetate

A mixture of 855 mg. (7.5 mmoles) potassium thioacetate and 1.27 g (5 mmoles) crude 2-pyrrolidon-3-yl-p-toluenesulfonate in 40 ml. acetone was refluxed under nitrogen for ca. 20 hr. The mixture was then filtered and the filtrate was concentrated in vacuo. The residue was partitioned between 50 ml. ethyl acetate and 50 ml.

water and the ethyl acetate layer was washed with 40 ml. water and 40 ml. saturated aqueous sodium chloride solution. The ethyl acetate solution was dried over anhydrous sodium sulfate and concentrated in vacuo. The crude product was chromatographed on silica gel, eluting with ethyl acetate, to yield 180 mg. (23% yield) of the title compound.

The NMR spectrum of the title compound as a deuterochloroform solution had peaks at 2.38 (s) and 1.7–2.98 (c) (total 5H); 2.27–3.6 (m, 2H); 4.17 (t, 1H); and 7.74 (b, 1H)ppm.

PREPARATION Q

The procedures of Preparation P were employed with the starting p-toluenesulfonates shown in Table 4 to obtain the corresponding thioacetates whose yield and NMR spectra as deuterochloroform solutions are shown.

TABLE 4

| p-Toluenesulfonate | Yield of corresponding thioacetate (%) | NMR(ppm) |
| --- | --- | --- |
| 2-pyrrolidon-4-yl | 61 | 2.34(s) and 2.0–4.4 (c) (total 8H); and 7.44 (b, 1H). |
| 1-formyl-3-pyrrolidinyl | 95 | 2.4(s) and 1.63–3.06 (c) (total 5H); 3.14–4.26 (c,4H); and 8.14 (b, 1H). |
| (3-methyl-1,3-oxazolidin-2-on-5-yl)methyl | 77 | 2.38(s, 3H); 2.82 (s,3H); 3.03–3.81 (c, 4H); and 4.57 (m, 1H). |
| (3-methyl-1,3-oxazolidin-2-on-4-yl)methyl | 68 | 2.36(s, 3H); 2.82(s) and 2.75–3.45(m) (total 5H); and 3.64–4.57 (c, 3H). |

PREPARATION R

Pyrrolidin-2,5-dion-3-yl Thioacetate

Maleimide (5.0 g., 0.051 mole) was added to 10 ml. (0.14 mole) thioacetate acid cooled to 0° C. under nitrogen. The mixture was stirred at 0° C. for 70 min., then filtered. The filtrate was diluted with 70 ml. ethyl acetate and the resulting solution was washed with 50 ml. saturated aqueous sodium bicarbonate solution and 50 ml. saturated aqueous sodium chloride solution. The ethyl acetate layer was dried over anhydrous sodium sulfate and concentrated in vacuo to a yellow oil (5.4 g). The crude product was purified by flash chromatography on silica gel (350 g.), eluting with 1:3 ethyl acetate-hexane, to yield 3.81 g (43%) of the title compound as a white solid. The NMR spectrum of the title compound as a deuterochloroform solution had peaks at 2.38 (s) and 2.3–3.54 (m) (total 5H); 4.24 (m, 1H); and 8.86 (b, 1H)ppm.

PREPARATION S

2-Piperidon-5-yl p-Toluenesulfonate

2-Piperidon-5-ol (0.575 g, 5 mmoles) was dissolved in 15 ml. dimethylformamide and the solution was diluted with 50 ml. dichloromethane. The solution was cooled to 0° C. under nitrogen and 0.95 g. (5 mmoles) p-toluenesulfonyl chloride and 1.22 g. (10 mmoles) 4-dimethylaminopyridine was added. The solution was stirred at 0° C. for 3 hrs., then at 25° C. for 20 hrs. The reaction mixture was then diluted with 125 ml. dichloromethane and the solution was washed with 20 ml. 1N aqueous hydrochloric acid solution, two 20 ml. portions of water and 20 ml. saturated aqueous sodium chloride solution. The organic layer was dried over anhydrous sodium sulfate and concentrated in vacuo. Diethyl ether was added to the residue and the title compound was obtained as the resulting solid product following filtration (0.8 g, 60% yield). The NMR spectrum of the title compound as a deuterochloroform solution had peaks at 2.4 (s) and 1.67–2.6 (c) (total 7H); 3.43 (c, 2H); 4.86 (m, 1H); 6.96 (b, 1H); 7.3 (d, 2H); and 7.76 (d, 2H)ppm.

PREPARATION T

2-Piperidon-5-yl Thioacetate

A solution of 1.9 g (6 mmoles) tetrabutylammonium thioacetate and 0.807 g (3 mmoles) 2-piperidon-5-yl p-toluenesulfonate in 15 ml. acetone was refluxed under nitrogen for 70 minutes. The solution was then concentrated in vacuo and the residue was dissolved in 75 ml. ethyl acetate. The ethyl acetate solution was washed sequentially with 10 ml. water, 10 ml. saturated aqueous sodium chloride solution, 10 ml. water and 10 ml. saturated aqueous sodium chloride solution. The combined aqueous extracts were washed with two 50 ml. portions of ethyl acetate. The combined ethyl acetate fractions were dried over anhydrous sodium sulfate and concentrated in vacuo. The crude product was chromatographed on silica gel (100 g.), eluting with ethyl acetate to yield 0.229 g (44%) of the title compound as a yellowish solid. The NMR spectrum of the title compound as a deuterochloroform solution had peaks at 2.4 (s) and 1.64–2.68 (c) (total 7H); 2.73–4.1 (c, 3H); and 7.05 (b, 1H)ppm.

PREPARATION U

(1,3-Oxazolidin-2-on-4-yl)methyl p-Toluenesulfonate p-Toluenesulfonyl chloride (1.01 g, 0.0053 mole) was added to a stirred solution of 2-oxo-1,3-oxazolidin-4-methanol (0.619 g, 0.0053 mole) and 4-dimethylaminopyridine (1.30 g, 0.0106 mole) in 60 ml. methylene chloride at 0° C. under an atmosphere of nitrogen. After 1 hour at 0° C., 0.121 g. more p-toluenesulfonyl chloride was added and the reaction mixture was stirred at 0° C. for 30 min. and at 25° C. for 1 hour. The reaction solution was then washed with two 50 ml. portions of 1N aqueous hydrochloric acid solution, 50 ml. water, 50 ml. saturated aqueous sodium bicarbonate solution and 50 ml. saturated aqueous sodium chloride solution, dried over anhydrous sodium sulfate and concentrated in vacuo to a white solid of the title compound (1.22 g, 85% yield). NMR (CDCl$_3$): 2.45 (s, 3H); 3.87–4.54 (c, 5H); 6.18 (b, 1H); 7.3 (d, 2H); and 7.73 (d, 2H)ppm.

PREPARATION V

Using the procedures of Preparation U, the appropriate starting material alcohol was converted to the corresponding tosylate whose R, yield and NMR spectrum are shown in Table 4.

TABLE 4

| R | NMR (ppm) | Yield (%) |
| --- | --- | --- |
| (1,3-oxazolidin-2-on-5-yl)methyl | 2.46 (s, 3H); 3.54 (m, 2H); 4.13 (d, 2H); 4.8 (m, 1H); 6.23 (b, 1H); 7.33 (d, 2H); and 7.8 (d, 2H). | 84 |
| (1,3-thiazolidin-2-on-4-yl)methyl | 2.45 (s, 3H); 3.32 (m, 2H); 3.86–4.32 | 88 |

| TABLE 4-continued | | |
|---|---|---|
| R | NMR (ppm) | Yield (%) |
| | (c, 3H); 6.06 (b, 1H); 7.32 (d, 2H); and 7.74 (d, 2H). | |

PREPARATION W

1-Methylpiperidin-2-on-3-yl Methylsulfonate

Methanesulfonyl chloride (0.8 ml., 0.01 mole) was added dropwise to a stirred solution of 1-methyl-2-oxo-3-piperidinol (1.29 g, 0.01 mole) and 4-dimethylaminopyridine (2.44 g., 0.02 mole), in 50 ml. methylene chloride at 0° C. under nitrogen. The resulting solution was stirred at 0° C. for 15 min. and at 25° C. for 2.5 hours. The reaction mixture was then washed with 50 ml. saturated aqueous sodium chloride solution containing 6.8 ml. of 6N aqueous hydrochloric acid solution, dried over anhydrous sodium sulfate and concentrated in vacuo to a thick oil of the title compound (1.8 g., 87% yield). NMR (CDCl$_3$): 1.6–2.37 (c, 4H); 2.96 (s, 3H); 3.1–3.4 (c) and 3.24 (s) (total 5H); and 4.9 (m, 1H)ppm.

In a similar manner 2-oxo-piperidin-3-ol was converted in 25% yield to piperidin-2-on-3-yl methylsulfonate. NMR (CDCl$_3$): 2.03 (c, 4H); 3.06–3.45 (c) and 3.25 (s) (total 5H); 4.96(m, 1H); 6.36(b, 1H)ppm.

PREPARATION X

(1,3-Oxazolidin-2-on-4-yl)methyl Thioacetate

A solution of 2-oxo-1,3-oxazolidin-4-ylmethyl p-toluenesulfonate (1.22 g., 0.0045 mole) and tetrabutylammonium thioacetate (1.71 g, 0.0054 mole) in 75 ml. acetone was refluxed under nitrogen for 90 min. The reaction mixture was concentrated to dryness and the residue was chromatographed on silica gel (250 g). Elution with 4:1 ethyl acetate-hexane yielded 580 mg. of the title compound (75% yield). NMR (CDCl$_3$): 2.38 (s, 3H); 3.06 (d, 2H); 3.84–4.67 (c, 3H); and 6.3 (b, 1H)ppm.

PREPARATION Y

Using the procedures of Preparation X, the appropriate p-tosylate was converted to the corresponding thioacetate whose R, NMR spectrum in deuterochloroform and yield are shown in Table 5.

TABLE 5

| R | NMR (ppm) | Yield (%) |
|---|---|---|
| (1,3-oxazolidin-2-on-5-yl)methyl | 2.37 (s, 3H); 3.22 (d, 2H); 3.47 (m, 2H); 4.7 (m, 1H); and 6.26 (b, 1H); | 76 |
| (1,3-thiazolidin-2-on-4-yl)methyl | 2.4 (s, 3H); 3.13 (d, 2H); 3.32 (m, 2H); 3.93 (m, 1H); and 6.63 (b, 1H). | 58 |
| 3-methyl-perhydro-1,3-oxazin-5-yl | 2.4 (s, 3H); 2.98 (s, 3H); and 3.0–4.6 (c, 5H). | 61 |

PREPARATION Z

1-Formyl-3-piperidinyl Thioacetate

A solution of 1-formyl-3-piperidinyl p-toluenesulfonate (1.12 g., 0.007 mole) and potassium thioacetate (0.91 g., 0.008 mole) in 10 ml. dimethylformamide was heated at 70° C. under nitrogen for 20 hours. The reaction mixture was diluted with 150 ml. ethyl acetate and the resulting solution was washed with four 50 ml. portions of water and 50 ml. brine, dried over anhydrous sodium acetate and concentrated in vacuo. The residue was chromatographed on silica gel (125 g.) eluting with 4:1 ethyl acetate-hexane to yield 0.16 g. (21% yield) of the title compound. NMR (CDCl$_3$): 1.13–2.3 (c) and 2.32 (s) (total 7H); 2.84–4.0 (c, 5H); and 7.9 (d, 1H)ppm.

PREPARATION AA

1-Methylpiperidin-2-on-3-yl Thioacetate

A mixture of 1-methyl-2-oxo-3-piperidinyl methanesulfonate (1.7 g., 0.008 mole) and potassium thioacetate (1.39 g., 0.012 mole) in 80 ml. acetone was refluxed under nitrogen for 20 hours. The reaction mixture was concentrated in vacuo and the residue was dissolved in 50 ml. ethyl acetate and 50 ml. water. The ethyl acetate layer was washed with 50 ml. water and 50 ml saturated aqueous sodium chloride solution, dried over anhydrous sodium acetate and concentrated in vacuo. The residue was chromatographed on silica gel eluting with ethyl acetate to yield 600 mg (40% yield) of the title compound. NMR (CDCl$_3$): 1.7–2.5 (c) and 2.38 (s) (total 7H); 3.0 (s, 3H); 3.36 (m, 2H); and 4.2 (m, 1H)ppm.

In a similar manner piperidin-2-on-3-yl methylsulfonate was converted to piperidin-2-on-3-yl thioacetate in 56% yield. NMR (CDCl$_3$): 1.5–2.5 (c) and 2.36 (s) (total 7H); 3.32 (c, 2H); 4.13 (m, 1H); 7.18 (b, 1H)ppm.

I claim:

1. A compound of the formula

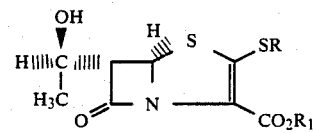

or a pharmaceutically acceptable salt thereof, wherein R is

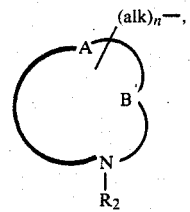

A is alkylene having 2–4 carbon atoms, alkylene having 2–4 carbon atoms wherein a carbon atom has an oxo substituent or alkylene having 2–4 carbon atoms wherein a methylene is replaced by oxygen or sulfur, B is carbonyl or methylene;

R$_1$ is hydrogen or forms an ester group which is hydrolyzed in vivo;

R$_2$ is hydrogen, formyl or alkyl having from one to four carbon atoms;

alk is alkylene having from one to four carbon atoms; and n is zero or one, with the proviso that when B is methylene and A is alkylene having 2–4 carbon atoms, alkylene having 2–4 carbon atoms wherein a carbon atom has an oxo substituent and said carbon atom is not adjacent to the nitrogen atom of R or alkylene having 2–4 carbon atoms wherein a methylene is replaced by oxygen or sulfur, R$_2$ is formyl.

2. A compound according to claim 1 wherein alk is methylene.

3. A compound according to claim 1 wherein A is alkylene, B is carbonyl, $R_2$ is hydrogen or methyl and n is zero.

4. A compound according to claim 3 wherein $R_1$ is hydrogen.

5. A compound according to claim 4 wherein R is 2-pyrrolidon-3-yl, 2-pyrrolidon-4-yl, piperidin-2-on-3-yl, 1-methylpiperidin-2-on-3-yl, or 2-piperidon-5-yl.

6. A compound according to claim 1 wherein A is alkylene, B is methylene, $R_2$ is formyl and n is zero.

7. A compound according to claim 6 wherein $R_1$ is hydrogen.

8. A compound according to claim 7 wherein R is 1-formyl-3-pyrrolidinyl or 1-formylpiperidin-3-yl.

9. A compound according to claim 1 wherein A is carbonylethylene or carbonylpropylene, B is carbonyl, and $R_2$ is hydrogen or methyl, with the proviso that the ethylene or propylene of A is bonded to B.

10. A compound according to claim 9 wherein $R_1$ is hydrogen.

11. A compound according to claim 10 wherein R is pyrrolidin-2,5-dion-3-yl.

12. A compound according to claim 1 wherein A is 1-oxaalkylene, B is carbonyl, $R_2$ is hydrogen or methyl and n is one, with the proviso that the oxygen of 1-oxaalkylene is bonded to B.

13. A compound according to claim 12 wherein $R_1$ is hydrogen.

14. A compound according to claim 13 wherein R is (3-methyl-1,3-oxazolidin-2-on-4-yl)methyl, (3-methyl-1,3-oxazolidin-2-on-5-yl)methyl, (1,3-oxazolidin-2-on-4-yl)methyl or (1,3-oxazolidine-2-on-5-yl)methyl.

15. A compound according to claim 1 wherein A is 1-thiaalkylene, B is carbonyl, $R_2$ is hydrogen or methyl and n is one.

16. A compound according to claim 15 wherein $R_1$ is hydrogen.

17. A compound according to claim 16 wherein R is (1,3-thiazolidin-2-on-4-yl)methyl.

18. A compound according to claim 1 wherein A is 1-oxaalkylene, B is carbonyl, $R_2$ is hydrogen or methyl and n is zero.

19. A compound according to claim 18 wherein $R_1$ is hydrogen.

20. A compound according to claim 19 wherein R is 3-methyl-perhydro-1,3-oxazin-2-on-5-yl.

21. A compound according to claim 1 wherein $R_1$ is hydrogen.

22. A compound according to claim 21 wherein R is 2-pyrrolidon-3-yl, 2-pyrrolidon-4-yl, 1-formyl-3-pyrrolidinyl, pyrrolidin-2,5-dion-3-yl, (3-methyl-1,3-oxazolidin-2-on-4-yl)methyl, (3-methyl-1,3-oxazolidin-2-on-5-yl)methyl, 2-piperidon-5-yl, piperidin-2-on-3-yl, 1-methylpiperidin-2-on-3-yl, 3-methyl-perhydro-1,3-oxazin-2-on-5-yl, 1-formyl-piperidin-3-yl, (1,3-oxazolidin-2-on-4-yl)methyl, (1,3-oxazolidin-2-on-5-yl)methyl or (1,3-thiazolidin-2-on-4-yl)methyl.

23. A pharmaceutical composition for control of a bacterial infection in a mammal comprising an antibacterial effective amount of a compound according to claim 1 and a pharmaceutically acceptable carrier or diluent.

24. A method of treating a bacterial infection in a mammal comprising administering an antibacterially effective amount of a compound according to claim 1.

* * * * *

UNITED STATES PATENT AND TRADEMARK OFFICE
CERTIFICATE OF CORRECTION

PATENT NO. : 4,772,597

DATED : September 20, 1988

INVENTOR(S) : Ernest S. Hamanaka

It is certified that error appears in the above-identified patent and that said Letters Patent is hereby corrected as shown below:

In the Abstract:

"R is 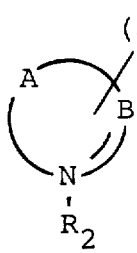 (alk)$\frac{}{n}$ " should read -- R is 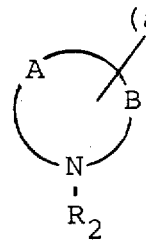 (alk)$\frac{}{n}$ --;

In the Specification:

Column 18, line 58:

"(0.01 mole)" should read -- (0.02 mole) --;

Column 20, line 11:

"7.778d, 2H)" should read -- 7.77 (d, 2H) --;

UNITED STATES PATENT AND TRADEMARK OFFICE
CERTIFICATE OF CORRECTION

PATENT NO. : 4,772,597

DATED : September 20, 1988

INVENTOR(S) : Ernest S. Hamanaka

It is certified that error appears in the above-identified patent and that said Letters Patent is hereby corrected as shown below:

Column 23, line 28:

"6.36 (b, 1H)ppm" should read -- 6.26 (b, 1H)ppm --;

Signed and Sealed this

Thirteenth Day of June, 1989

Attest:

DONALD J. QUIGG

*Attesting Officer*  *Commissioner of Patents and Trademarks*